US012343349B2

(12) United States Patent
Conesa Zamora et al.

(10) Patent No.: US 12,343,349 B2
(45) Date of Patent: Jul. 1, 2025

(54) IMIPRAMINE FOR USE AS AN INHIBITOR OF FASCIN1 OVEREXPRESSION

(71) Applicants: FUNDACION UNIVERSITARIA SAN ANTONIO, Guadalupe (ES); FUNDACION PARA LA FORMACIÓN E INVESTIGACIÓN SANITARIAS, Murcia (ES); UNIVERSIDAD DE GRANADA, Granada (ES)

(72) Inventors: Pablo Conesa Zamora, Murcia (ES); Horacio Perez Sanchez, Guadalupe (ES); Irene Luque Fernández, Granada (ES); Silvia Montoro García, Guadalupe (ES); Begoña Alburquerque Gonzalez, Guadalupe (ES); Priscila Campioni Rodrigues, Oulu (FI); José García Solano, Murcia (ES); Angel Bernabé García, Murcia (ES); Francisco José Nicolás Villaescusa, Murcia (ES); Manuel Bernabé García, Murcia (ES); Maria Luisa Cayuela Fuentes, Murcia (ES); Javier Ruiz Sanz, Granada (ES); Jose Cristobal Martínez Herrerías, Granada (ES); Tuula Salo, Helsinki (FI)

(73) Assignees: FUNDACION UNIVERSITARIA SAN ANTONIO, Granada (ES); FUNDACION PARA LA FORMACIÓN E INVESTIGACIÓN SANITARIAS, Murcia (ES); UNIVERSIDAD DE GRANADA, Granada (ES)

( * ) Notice: Subject to any disclaimer, the term of this patent is extended or adjusted under 35 U.S.C. 154(b) by 1040 days.

(21) Appl. No.: 17/281,084

(22) PCT Filed: Sep. 22, 2019

(86) PCT No.: PCT/ES2019/070631
§ 371 (c)(1),
(2) Date: Mar. 29, 2021

(87) PCT Pub. No.: WO2020/065113
PCT Pub. Date: Apr. 2, 2020

(65) Prior Publication Data
US 2023/0330096 A1    Oct. 19, 2023

(30) Foreign Application Priority Data
Sep. 28, 2018   (EP) ...................................... 18382696

(51) Int. Cl.
*A61K 31/55*      (2006.01)
*A61P 35/00*      (2006.01)
(52) U.S. Cl.
CPC .............. *A61K 31/55* (2013.01); *A61P 35/00* (2018.01)
(58) Field of Classification Search
CPC ................................ A61K 31/55; A61P 35/00
See application file for complete search history.

(56) References Cited

U.S. PATENT DOCUMENTS 9,573,946 B2 *   2/2017   Huang .................... A61P 37/02

OTHER PUBLICATIONS

R. Kraft et al: "A cell-based fascin bioassay identifies compounds with potential anti-metastasis or cognition-enhancing functions", Disease Models & Mechanisms, vol. 6, No. 1, Aug. 23, 2012 (Aug. 23, 2012), pp. 917-925.*

* cited by examiner

*Primary Examiner* — Kamal A Saeed
(74) *Attorney, Agent, or Firm* — Maier & Maier, PLLC (57) ABSTRACT

The present invention refers to Imipramine for use as inhibitor of fascin1 overexpression, preferably said overexpression of fascin1 is associated to cancer, and more preferably to colorectal cancer. It also refers to a method for the treatment of cancer mediated by fascin1 comprising administering to a subject in need thereof an effective amount of imipramine, and more preferably to colorectal cancer.

6 Claims, 9 Drawing Sheets
Specification includes a Sequence Listing.

IMIPRAMINE FOR USE AS AN INHIBITOR OF FASCIN1 OVEREXPRESSION

FIELD OF THE INVENTION

The present invention relates to the field of medicinal products, particularly to therapeutic products against cancer.

STATE OF THE ART PRIOR TO THE INVENTION

The identification of molecular targets is one of the greatest advances in recent cancer treatment. These therapies aim to block specific proteins that are altered in cancer and responsible for the tumor phenotype. Tumor metastasis remains the leading cause of cancer mortality (Chen, Yang, Jakoncic, Zhang, & Huang, 2010) and the prior acquisition of invading capacity is a prerequisite for carcinoma cells to get access to vessels and thus spread throughout the body. This process involves actin cytoskeleton rearrangement that allow the tumor cells to develop cellular protrusions, such as filopodia and invadopodia, which contribute to cancer cell migration, invasion, and metastasis (Machesky & Lia., 2010). Fascin1 is a key protein in filopodia and invadopodia formation as it possesses actin-binding and actin-bundling activity by cross-linking filamentous actin into tightly packed parallel bundles. Fascin1 is absent in most normal epithelia but expressed in many human carcinomas (Hashimoto, Kim, & Adams, 2011) and several previous studies have nominated this protein as a candidate biomarker for aggressive carcinomas. In fact, several studies including a meta-analysis have demonstrated that fascin1 expression is associated with increased lymph-node and distant-metastasis, disease progression and mortality in colorectal and breast cancer (Tan, Lewis, Adams, & Martin, 2013).

Colorectal cancer (CRC) is the third leading cause of cancer-related deaths in men and women in the United States. There are several ways to treat colorectal cancer, depending on its type and stage. As general rule, localized tumor is resected if there are not distant metastases or complication. If there is node affection, chemotherapy can be administered and in the case of rectal cancer pre-operation radiotherapy (neoadjuvant) therapy is recommended. If distant metastasis exists chemotherapy and monoclonal antibodies is the key treatment associated with radiotherapy and/or surgery in some occasions.

There are three type of pharmacological therapy in cancer:
a) Chemotherapy, which targets proliferating cells including, but not restricted to, cancer cells. Common chemotherapy in CRC includes 5-fluorouracil, capecitabine, oxaliplatine, irinotecan and raltitrexed.
b) Immunotherapy, which targets specific altered molecules in cancer by means of monoclonal antibodies (MAbs) or recombinant fusion proteins and includes cetuximab, panitumumab, bevacizumab and aflibercept. Cetuximab and panitumumab are Mabs targeting the epidermal growth factor receptor (EGFR) which are only useful in those CRC with no mutation on KRAS, NRAS and BRAF oncogenes. Bevacizumab, in turn, is a MAb against the vascular endothelial growth factor A (VEGF-A). Aflibercept is a fusion protein against VEGF-A and VEGF-B. Finally pembrolizumab is a MAb against the immune chekpoint and is effective in those CRCs showing microsatellite instability (MSI)
c) Tyrosine kinase inhibitors (TKI) are orally administered and in CRC are represented by regorafenib proven to be effective in metastatic CRC resistant to standard therapies.

Serrated adenocarcinoma (SAC) has been recently recognized in the latest WHO classification of tumors of the digestive system as a new subtype of CRC (Hamilton, 2010). Criteria for its histologic diagnosis have been proposed and recently validated in a series of 81 cases. The SAC frequency ranges from 7.5 to 8.7% of all CRCs and it has been shown to have a worse prognosis than conventional carcinoma (CC). Accordingly, SAC displays a higher frequency of adverse histological features at the invasive front including high-grade tumor budding and cytoplasmic pseudofragments, infiltrating growth pattern and weak peritumoral lymphocyte response. More recently, an immunohistochemical study on adhesion molecules has demonstrated a different expression pattern of SAC compared to CC. Consistent with previous evidence, two previous studies on mRNA profiling studies including ours, have revealed that SAC showed a higher representation of activation of morphogenesis-, hypoxia-, cytoskeleton- and vesicle transport-related functions and also as well as the over-expression of HIF-1α(a hypoxia-inducible factor), the antiapoptotic gene hippocalcin and fascin1 (actin-bundling protein associated with invasion) compared to conventional carcinoma (CC) (Conesa-Zamora et al., 2013; Laiho et al., 2007; Tuomisto et al., 2016). Moreover, fascin1 was found to be the most discriminatory marker in distinguishing SAC from CC with an immunohistochemical overexpression in the former of 88.6% compared to 14.3% in CC. Even tumors showing histological and molecular features of microsatellite instability displayed lower fascin1 expression than SAC (50%) and qPCR assays analyzing the expression of fascin1 in these CRC supbtypes also confirmed these findings (Conesa-Zamora et al., 2013).

Given the causative role of fascin1 in the invading phenotype of tumor cells and its overexpression associated with worse survival in a wide variety of cancer types (Tan et al., 2013) including many with no tailored molecular therapy as triple-negative breast carcinoma, it is mandatory to obtain efficient fascin1 blockers. In this line, migrastatin and its macroketone analogues are considered typical fascin1 inhibitors thus decreasing metastatic tumor cell migration, invasion and tumor metastasis (Chen et al., 2010) despite the fact that their complex structure hinders the process of synthesis. Some authors have reported an anti-fascin1, anti-migratory and anti-invasive activity for compounds derived from indazol-furan-carboxamides (Han et al., 2016).

WO2015127125 (A1) provides compounds of the general formula.

compositions and methods for inhibiting fascin1 activity or treating a condition or disorder mediated by fascin1 activity in a subject in need thereof.

Hereafter, there is an urgent need to identify other kind of drugs with novel anti-fascin1 activity.

Two independent studies, including ours on Finnish and Spanish population, have demonstrated that SACs show a higher frequency of KRAS and BRAF mutations compared to conventional colorectal adenocarcinoma (Garcia-Solano et al., 2012; Stefanius et al., 2011) thus making SAC more resistant to anti-EGFR therapy in which effectiveness is obtained when KRAS and BRAF are non-mutated. In addition, SACs are mostly microsatellite stable and therefore cannot benefit from immune checkpoint inhibitors such as pembrolizumab. Given the high expression of fascin1 in SAC and the causative role of fascin1 in invasion and metastasis it has been found that imipramine is useful for treating SAC and other tumors overexpressing fascin1.

Imipramine is an antidepressant and FDA-approved compound for the treatment of depression.

According to the present invention it has surprisingly been found that imipramine is a compound that is effective in the treatment of CRC; and preferably in the treatment of serrated adenocarcinoma. Imipramine is a compound that is effective in the treatment of tumors overexpressing fascin1.

DESCRIPTION OF THE INVENTION

The present invention refers to imipramine for use as inhibitor of fascin1 overexpression.

Imipramine is the compound named 3-(10,11-dihydro-5H-dibenzo[b,f]azepin-5-yl)-N,N-dimethylpropan-1-amine, of chemical formula of $C_{19}H_2N_2$.

According to the present invention, preferably, the overexpression of fascin1 is associated to the presence of cancer.

According to particular embodiments of the invention, the cancer is colorectal cancer.

According to a preferred embodiment the colorectal cancer is serrated adenocarcinoma.

According to an additional preferred embodiment the colorectal cancer is metastatic colorectal cancer.

The present invention also refers to a composition comprising imipramine for use as inhibitor of fascin1 overexpression.

The present invention also refers to a method for treating cancer mediated by fascin1 comprising administering to a subject in need thereof an effective amount of imipramine. As used herein "treating" means one or more of preventing, curing, managing, reversing, attenuating, alleviating, minimizing, suppressing, or halting the deleterious effects of the above-described diseases.

According to particular embodiments of the method, the fascin1 is overexpressed.

According to particular embodiments of the method the cancer is colorectal cancer.

According to preferred embodiments of the method the colorectal cancer is serrated adenocarcinoma.

According to additional preferred embodiments of the method, the colorectal cancer is metastatic colorectal cancer The colorectal cancer can also be selected from gastrointestinal stromal tumors, leiomyosarcomas or melanomas.

EXAMPLES

With the aim of finding new anti-fascin1 compounds we carried out a funnel-like workflow in which in silico compound library screening rendered selected molecules for their potential to bind fascin1 which were subsequently evaluated in vivo by a physical chemistry assay for their real interaction with fascin1. Those compounds binding fascin1 were tested in colorectal cell lines for their activity to avoid both lamelipodia formation and fascin1 location in these actin structures. Afterwards, migration and invasion assay using colorectal cancer cell lines were performed to test the compounds activity including the use of a myoma organotypic invasion model in which a benign human tumor stromal tissue was used to seed colorectal cancer cells in order to test their grade of invasion and the effect of fascin1 inhibitors. Finally, a living animal model of zebra fish larvae was used to assess tumor invasion. All these experiments which are explained below confirm that imipramine is a compound with fascin1 binding activity and with anti-migratory and anti-invasion effect in in vitro and in vivo assays.

Virtual Screening

Figure 1:
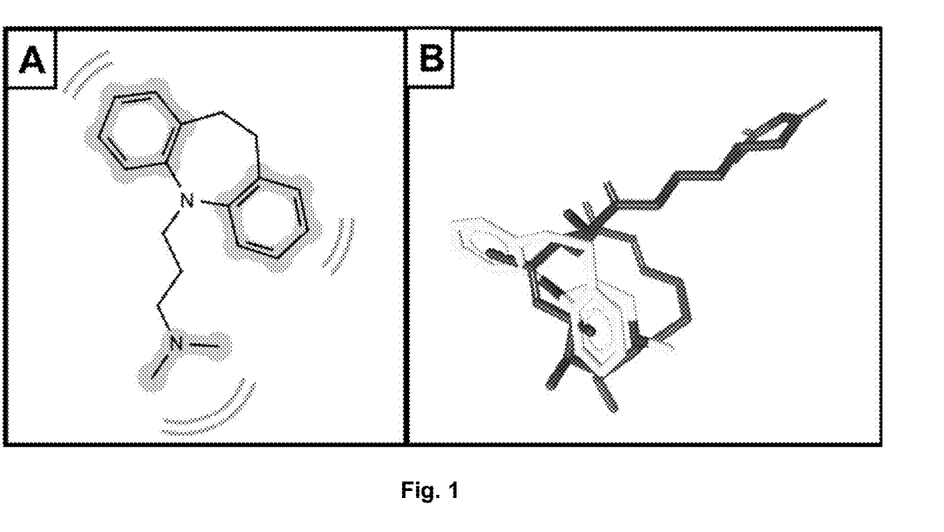
FIG. 1 shows the pharmacophoretic models for imipramine estimated using LigandScout Software.

Virtual Screening techniques were applied in order to propose compounds that might have better fascin1 inhibitory properties than migrastatin. Pharmacophoric modeling was applied to the core of the structure of migrastatin (MGS_CORE), previously characterized as can be seen in the formula below:

A ligand based pharmacophore model was derived from MGS_CORE using the Ligand Scout (LS) program (Gerhard Wolber, 2005). This model was screened against a subset of the DrugBank library (version 5.0; of 9,591 compounds including 2,037 approved by the American Food and Drug Administration (FDA), 96 nutraceuticals and 6000 experimental) after the fine tunning on a High Performance Computing (HPC) cluster of all related necessary programs from the LS suite. From resulting calculations and after careful visual inspection of the results and taking into account previous insights from literature, molecule imipramine was selected for posterior experimental validation. In FIG. 1A the pharmacophore model for imipramine is depicted. A 2D diagram of matching pharmacophoric features between MGS and imipramine is shown. 3D alignment of MGS (dark grey) and imipramine (light grey) is shown in FIG. 1.B.

Thermofluor

Figure 2A:
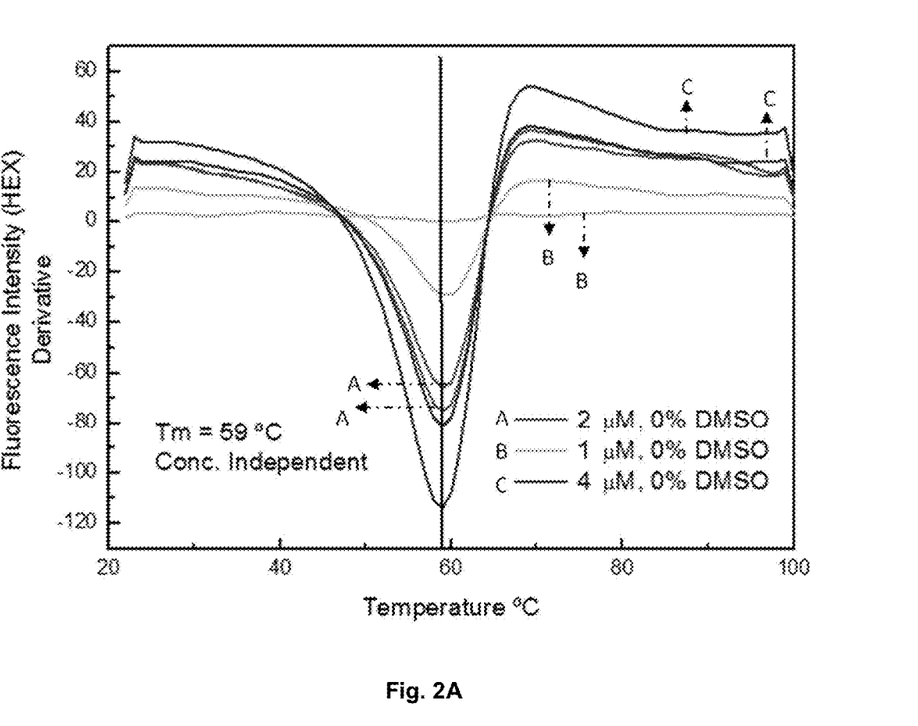
FIG. 2 shows Differential Scanning Fluorimetry assay. (A). Thermofluorometric derivative curves which allowed setting up fascin1 concentration at 2 µM. (B). Representation showing that imipramine stabilized fascin1 with a significant Tm chasing around 2° C. in replicates and using different fluorescence probes.
Figure 2B:
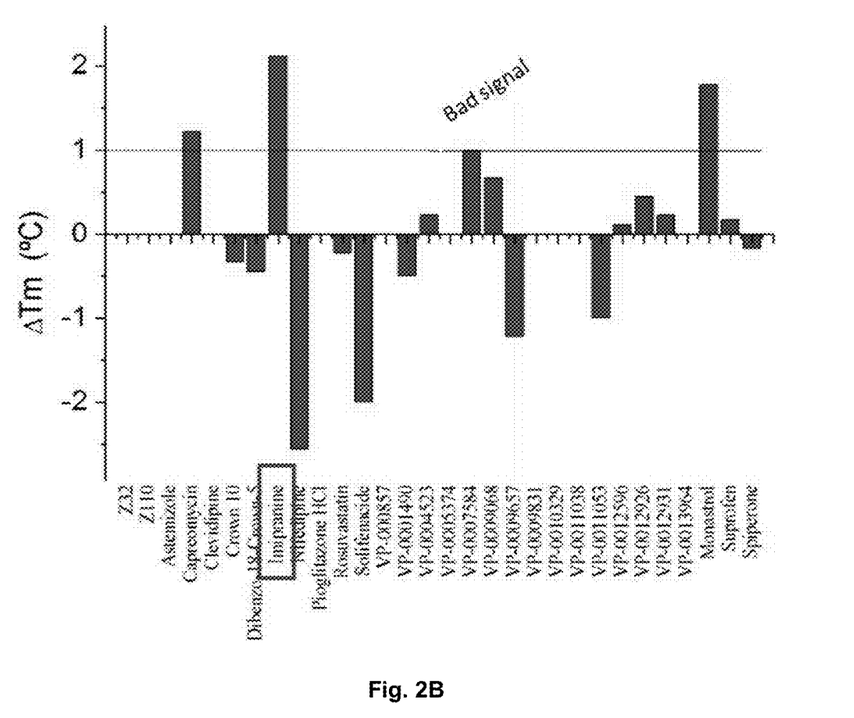

Differential Scanning Fluorimetry (Thermofluor) assays were performed using a Biorad C1000 Touch Thermal Cycler CFX96 RT-PCR system in a 96-well format. 25 µL reaction mixtures were set up containing 2 µM fascin1 (cat. No. 8411-02, Hypermol, Bielefeld, Germany) in 20 mM Hepes, 150 mM NaCl, 1 mM DTT and 5% sucrose at pH 7.4, in the presence of SYPRO Orange (1000-fold dilution from the commercial stock (Invitrogen) FIG. 2A shows the thermofluorometric derivative curves which allowed to set up fascin concentration at en 2 µM. FIG. 2B is a representation showing that imipramine stabilised fascin1 with a significant Tm chasing around 2° C. both in replicates and using different fluorescence probes.

Imipramine was prepared at 10 mM in 100% DMSO and added to each well to a final concentration of 1 mM and 10% DMSO. Three replicates with six internal controls, containing only free protein in 10% DMSO, were included in the 96-well plates. The PCR plates were covered and subsequently shaken, centrifuged, incubated for 2 min at 20° C. inside the RT-PCR machine and heated from 20 to 100° C. at a 1° C./min scan-rate. Fascin1 thermal denaturation profiles were obtained recording the fluorescence intensity for the FAM, HEX and T-Red predefined filters. The derivative of the fluorescence curve was used to determine the Tm. Changes in Tm associated to ligand binding were estimated taking the average Tm value derived from the free protein internal controls.

Fluorescence Titration

Fascin1 was extensively dialized against the appropriate buffer prior to each titration experiment. Fascin1 concentration was determined by measuring absorbance at 280 nm using an extinction coefficient of 67840 cm-1-M-1. Fluorescence titration experiments were performed in a Cary Eclipse spectrofluorimeter (Varian Inc.). A 15 µM (14.7 µM) fascin1 solution was titrated with each compound by adding increasing volumes of concentrated solutions. Emission spectra were recorded between 307 and 500 nm at 25° C. in 10% DMSO, 100 mM NaCl, 20 mM Hepes, pH 7.4, with the excitation wavelength fixed at 280 nm. Binding isotherms were generated using either the changes in spectral area or in spectral centre of mass (CM), depending whether the change was only in fluorescence intensity or was also in the maximum emission wavelength.

The resulting curves were fitted using ORIGIN 7.0 (Microcal Inc.) and a one-site equilibrium binding model, according to the following equation:

$$F = F_f + (F_b - F_f) \cdot \frac{(P_T + L_T + K_d) - \sqrt{(P_T + L_T + K_d)^2 - 4 \cdot P_T \cdot L_T}}{2 \cdot P_T}$$

Ff and Fb are the fluorescence signal (area or CM) of free and bound fascin1 and PT and LT are the total protein and ligand concentration, respectively, at each addition point. Tm values were measured as the minimum of the first derivative of the thermal unfolding profile. Average Tm values for unbound fascin1 were obtained for each internal filter (FAM, HEX and T-Red) as reference for the determination of the changes in Tm upon compound binding (Tm,FAM=55.6±0.5° C., Tm,HEX=56.0±0.0° C., Tm,Tred=56.2±0.6° C., where the error values correspond to the standard deviation for the seven replicas included in each plate as internal controls).

The results of the Thermal Shift Assay are summarized in Table 1. Some compounds resulted in distorted thermal unfolding profiles from which reliable Tm values could not be extracted, probably due to compound interference with the Sypro fluorescence signal. Within those that could be analyzed, imipramine consistently resulted in a significant increase in Tm, of about 2° C., suggesting specific binding to fascin1 (FIG. 2B). Binding of these compounds to fascin1 was validated in vitro using fluorescence titration experiments, rendering dissociation constants in the high microMolar range (Kd=390 µM for imipramine).

TABLE 1

Thermal Shift Assay Results

| Compound | Conc (mM) | $T_{m, FAM}$ (° C.) | $\Delta T_{m, FAM}$ (° C.) | $T_{m, HEX}$ (° C.) | $\Delta T_{m, HEX}$ (° C.) | $T_{m, TRed}$ (° C.) | $\Delta T_{m, TRed}$ (° C.) |
|---|---|---|---|---|---|---|---|
| Free fascin1 | — | 55.7 ± 0.5 | — | 56.0 ± 0.0 | — | 56.2 ± 0.6 | — |
| Imipranine | 1 | 58.3 ± 0.6 | 2.7 ± 1.1 | 58.0 ± 0.0 | 2.0 ± 0.0 | 58.0 ± 0.0 | 1.8 ± 0.6 |

Cell Culture

Three human colorectal adenocarcinoma cell lines were obtained from the American Type Culture Collection (ATCC, Rockville, MD): HCT116, SW480 and DLD1. The cell lines were cultivated in high glucose Dulbecco's Modified Eagle's Medium (DMEM) containing 10% heat-inactivated fetal bovine serum (FBS), 50 U/ml penicillin and 50 µg/ml streptomycin (Sigma Aldrich Chemical Co., USA) in an atmosphere of 5% $CO_2$ and 95% humidified air at 37° C. Subculture was performed when 90% confluence was obtained. Fascin1 gene expression was measured following the protocol previously described [Conesa-Zamora IJC]. RNA was extracted by treating cell line pellets around 200,000 cells with 700 µl of Qiazol (Qiagen ref: 1023537) and by adding 140 µl of chloroform and centrifuging at 12,000 g for 15 min at 4° C. The aqueous phase containing 350 µl was then subjected to automatic total RNA extraction using the Qiacube equipment and the miRNeasy Mini Kit (ref: 217004), both provided by Qiagen. cDNA was obtained using the Maxima First Strand cDNA Synthesis Kit for RT-qPCR by Thermo Fisher (cat. No. K1671) following the manufacturer information. Five microlitres of 1:5 diluted cDNA was added to the qPCR reaction containing 12.5 µl 2× QuantiTect SYBR Green PCR Kit (ref:204145) by Qiagen and 300 nM of each primer in a total volume of 25 µl. qPCR was performed on a 7500 F real time PCR system by Applied Biosystems (Foster City, CA, USA) according to the instruction manual and following the standard protocol: 50° C. 2 min, 95° C. 10 min, 40 cycles of 95° C. 15 sec, 60° C. 1 min and a melt curve stage consisting in 95° C. 15 sec, 60° C. min, 95° C. 30 sec and 60° C. 30 sec. The relative quantitation was done by the 2-ΔCt method using β-actin as housekeeping gene. The amounts of mRNA are given as number of copies per million of copies of β-actin. Primers of β-actin used for FSCN quantitation were 115F and 116R whereas those for HPCA and DAG1 were b-a-blgF and b-a-blgR.

TABLE 2

Primer sequences used for quantitative PCR validation (Gene, Primer name, Primer sequence (5'-3'), size (bp).

| fragment Gene | Primer name | Sequence (5'-3') | Fragment size (bp) |
|---|---|---|---|
| FSCN1 (ENSG00000075618) | 115F | TCCACGCGCCA GGG-TATGGAC (SEQ ID NO.: 1) | 121 |
|  | 116R | ACTTGCCCGT GTGGG-TACGG (SEQ ID NO.: 2) |  |
| β-ACTIN (ENSG00000075624) | b-a-blgF | GAGCTAC-GAG CTGCCTGACG (SEQ ID NO.: 3) | 120 |
|  | b-a-blgR | GTAGTTTCGTG-GATGCCACAG (SEQ ID NO.: 4) |  |

Figure 3:
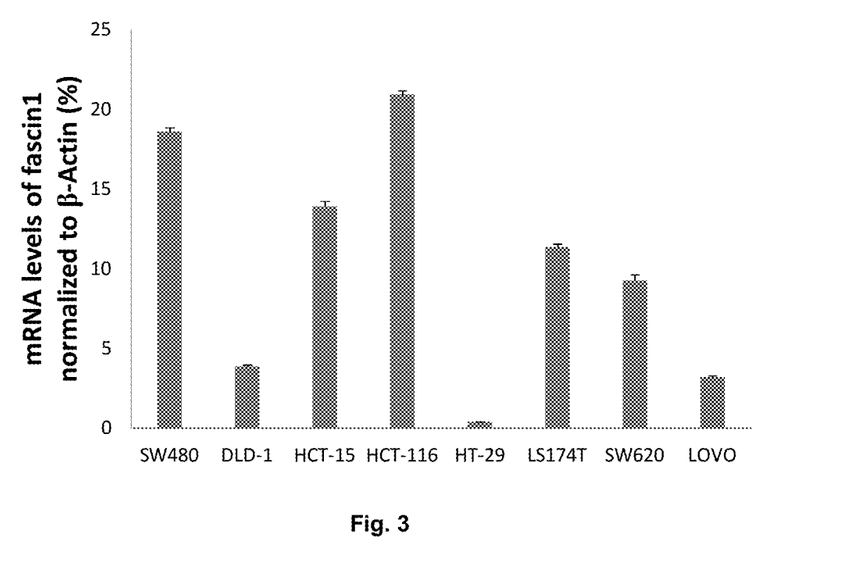
FIG. 3 shows the mRNA expression levels of fascin1 in eight colorectal cell lines using a β-actin gene expression for data normalizing. HCT-116 and SW-480 shows the highest fascin1 expression whilst LOVO, DLD-1 and HT-29 show the lowest.

In order to choose colorectal cell lines with highest and lowest endogenous fascin1 expression, a RT-qPCR was performed upon RNA extracted from eight cell lines. FIG. 3 illustrates how HCT-116 and SW-480 shows the highest fascin1 expression whilst LOVO, DLD-1 and HT-29 show the lowest. Given the ease for cell culture and the suitable morphology with prominent cytoplasm for immunofluorescence, migration and invasion assessment we selected DLD-1, SW-480 and HCT-116 cell lines in the subsequent assays.

Cell Viability Assay

Figure 4A:
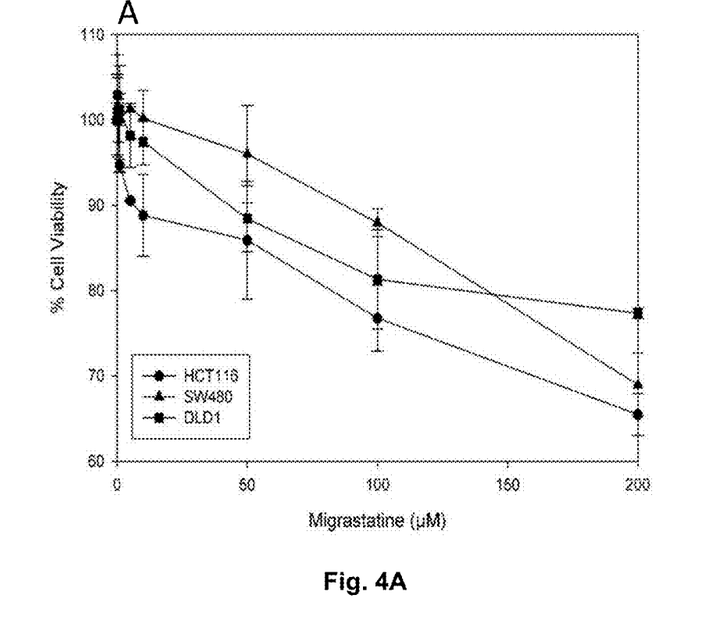
FIG. 4 shows the colorectal cell line viability assay. The effect of migrastatin (A); imipramine (B) on the cell viability of DLD-1, HCT-116 and SW480 colorectal cell lines is shown.
Figure 4B:
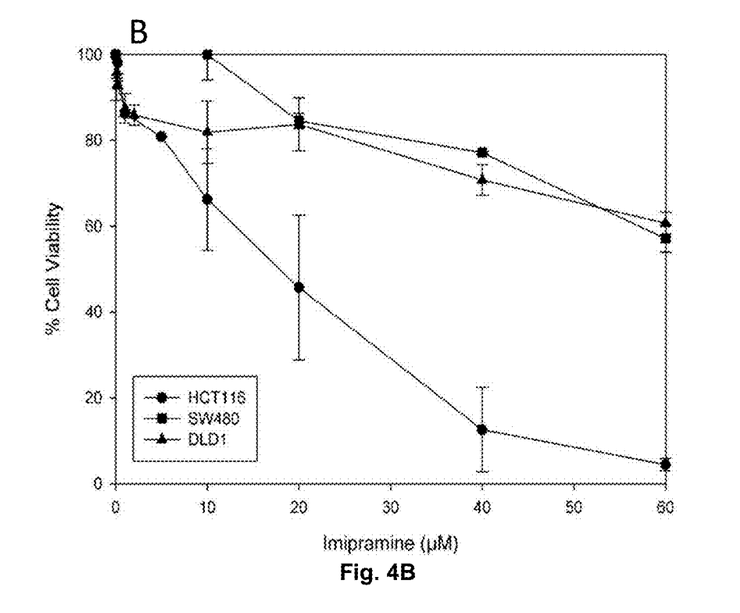

Exponentially growing cells were plated in triplicate in flat-bottomed 96-well plates (Nunc, Roskilde, Denmark) at 1200 cells/well. The day after, drugs were added in serial dilution from 5100 nM to 3100 µM. Control wells contained medium without drug plus 0.1% DMSO. Plates were incubated for 3 days in a humidified 5% $CO_2$ incubator and assayed for cell viability. Tetrazolium (MTT) dissolved in phosphate-buffered saline (PBS), pH 7.2, at 1.9 mg/mLI was added to the cells (30 µl/well). After incubation at 37° C. for 4 h, the medium was aspirated. The formazan crystals were dissolved in 200 µL dimethyl sulfoxide (DMSO) for 30 min and the absorbance was read at 570 nm in a microtitre plate reader. Results were calculated as: cell viability (%)=average O.D. of wells/average O.D. of control wells 1. The 50% inhibitory concentration (IC50) for a particular drug was defined as the concentration producing 50% decrease in cell growth. FIG. 4 shows the effect of migrastatin (A) and imipramine (B) on the cell viability of DLD-1, HCT-116 and SW480 colorectal cell lines. According to data presented in FIG. 4, the working concentration of imipramine and migrastatin was set up for subsequent in vitro studies at 20 µM and 100 µM, respectively.

Immunofluorescence

In order to assess the effect of imipramine on fascin1 localization and lamelipodia formation an immunofluorescence assay was performed. Round coverslips (Thermo Fisher, Waltham, MA USA) were seeded with HCT116 cell line in the presence of 10% FBS. After cells reached 100% confluence, serum supplemented medium was removed and replaced with fresh serum free medium for 24 h. Artificial wounding was performed by transversally dragging a sterilized razor blade on the central area of the coverslips. Coverslips were then placed in 6-well plate with 2 mL serum free DMEM and 100 µM migrastatin, 20 µM imipramine, Epidermal Growth Factor (EGF) 10 ng/ml and MEK inhibitor PD98059 50 µM (MEKi) (both from Sigma-Aldrich, St Louis, MO, USA) for 24 h. Cells were then fixed with Bouin (for fascin1 protein) or 4% formaldehyde (for actin protein) and subsequently permeabilized in a 0.3% Triton X-100/PBS solution, and then exposed to blocking buffer for 30 min. Samples were incubated for 1 h with anti-fascin1 antibody (1/250) (55K-2 clone; Santa Cruz Biotechnology, Heidelberg, Germany) or anti-β actin antibody (1/1000) (Sigma-Aldrich, St Louis, MO, USA) in a wet chamber.

Figure 5:
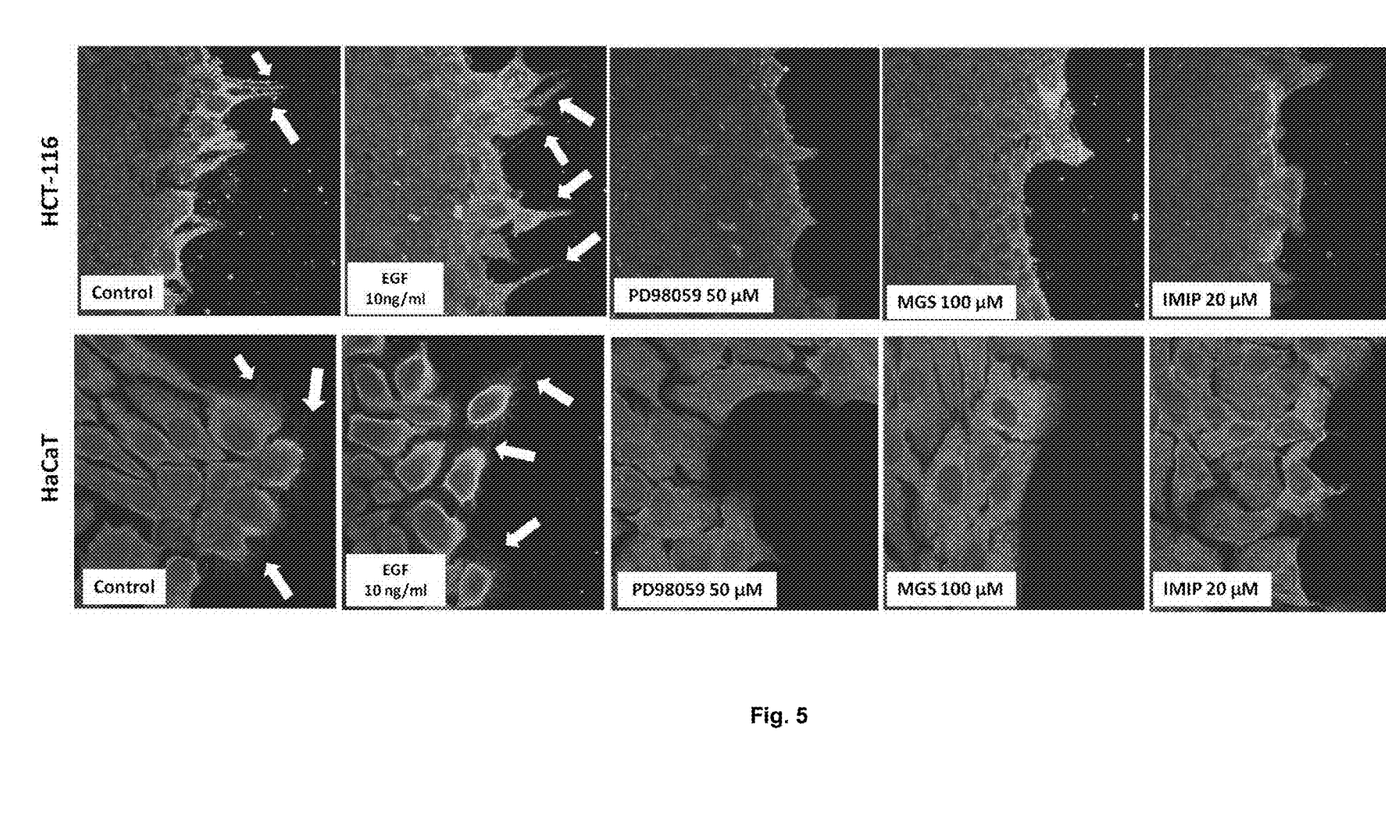
FIG. 5 shows the immunofluorescence of fascin1 in two cell lines; HCT-116 and a non tumoral cell line derived keratinocyte cell line HaCaT. It shows the immunofluorescence of fascin1 upon inhibition of filopodia formation.
Figure 6A:
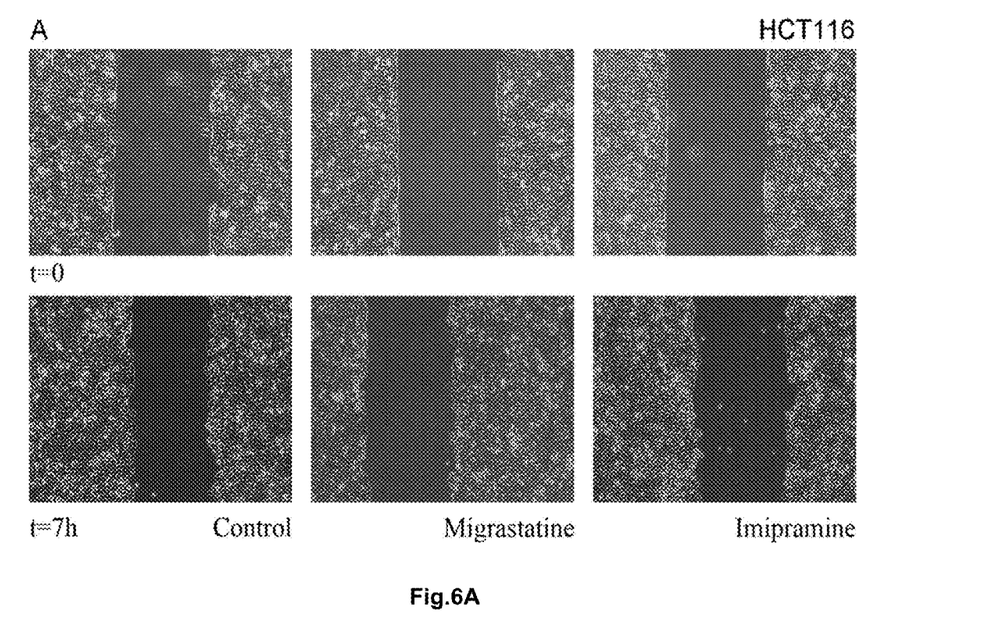
FIG. 6 shows the inhibition of three cell lines by imipramine and migrastatin A) HCT-116, B) DLD-1, C) SW-480, D) Migration was calculated with respect to the control conditions in lineal phase.
Figure 6B:
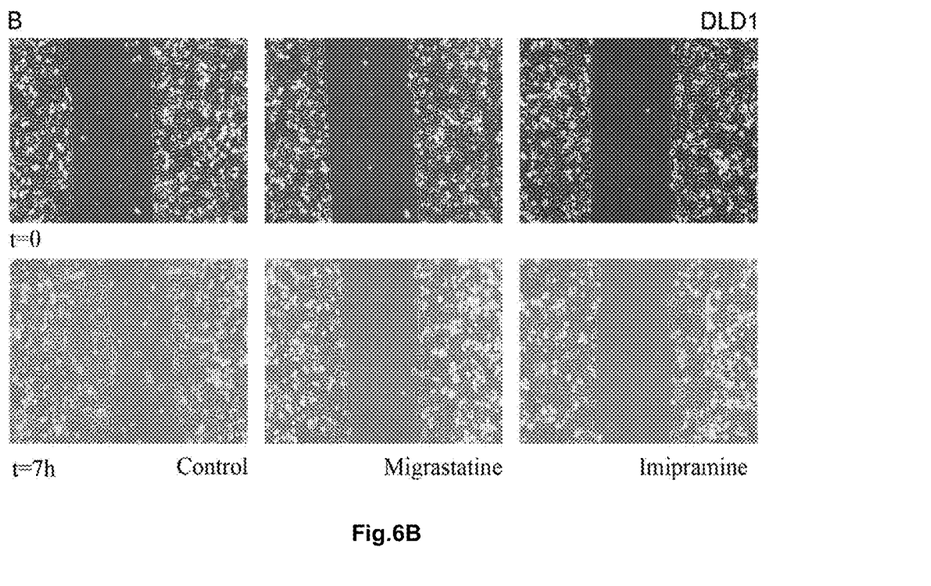
Figure 6C:
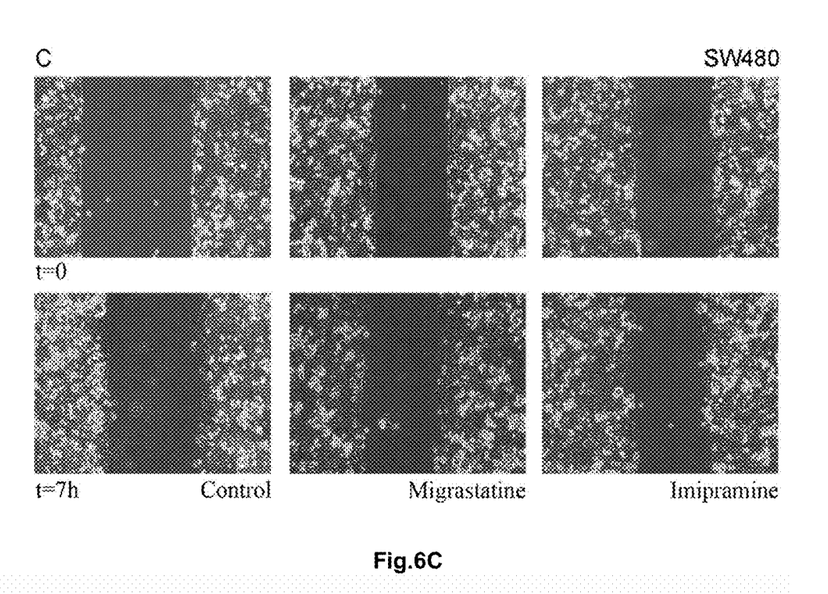
Figure 6D:
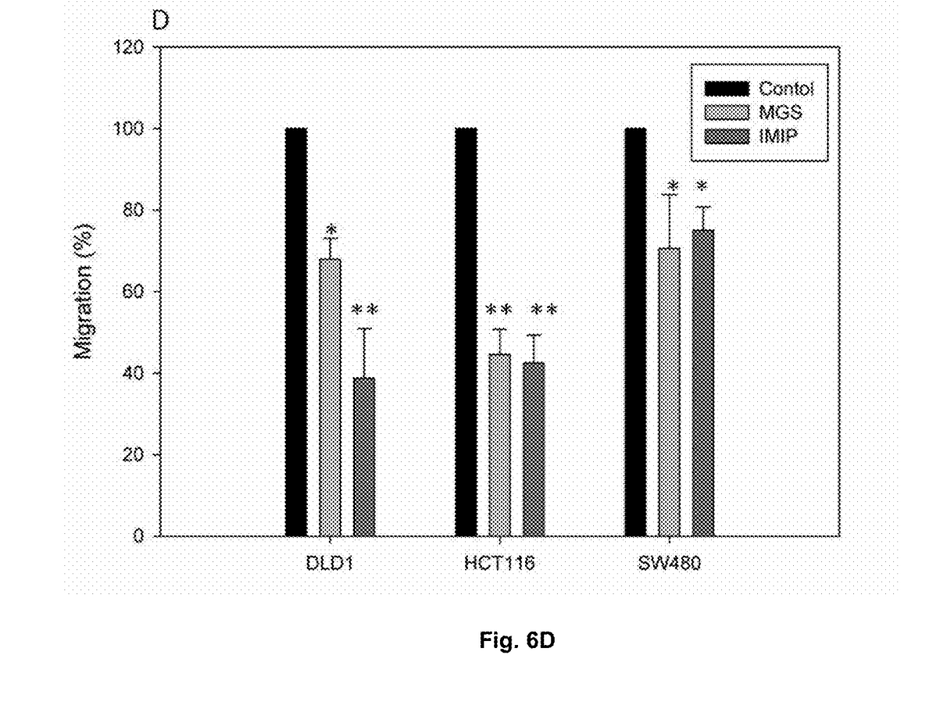

Appropriate fluorescent-labelled primary antibodies were incubated later with Alexa fluor 488-conjugated anti-mouse IgG (from donkey) (1/400) or Alexa fluor 594-labelled phalloidin, respectively (1/1000) (Molecular Probes, Thermo Fisher Scientific, Waltham, MA USA) and Hoechst 33258 (Fluka, Biochemika, Sigma-Aldrich, St Louis, MO, USA) for 30 min at room temperature and darkness. Samples were examined and representative images were taken with a confocal microscope (LSM 510 META from ZEISS, Jena, Germany). The effect of imipramine on the fascin1 localization and the reorganization of the actin cytoskeleton, which includes the protrusion of the lamellipodium at the cell front filopodia formation and fascin1 localization, was assessed by immunofluorescence. FIG. 5 shows the immunofluorescence of fascin1 in two cell lines; the cell line expressing higher fascin1 level, HCT-116 and a non tumoral cell line derived keratinocyte cell line HaCaT which was used as a control of the immunofluorescence stainin. A prominent filopodia lamellipodium formation was observed for in control conditions and for both MOCK and EGF treated cells whereas these cytoskeleton structures were absent in those cells treated with migrastatin and imipramine similarly to what observed with the migration inhibitor targeting Mek pathway, PD98059.

Lamellipodia protrusion number was calculated in the different conditions, being significantly lower after migrastatin, and imipramine treatments (data not shown).

In FIG. 5 the cell morphology of HCT-116 and HaCaT (as an example of cells that form cytoplasmic protrusions) of upon inhibition of filopodia formation is shown. Inset shows immunofluorescence analysis of the filopodia marker fascin (green protrusions indicated in arrows) upon control condition, 100 uM migrastatin, 20 µM imipramine, and 100 ng/ml Epidermal Growth Factor (migration stimulator). Images were captured with a LSM 510 META confocal fluorescence microscope with 63×oil objective. Migrastatin and imipramine inhibit lamellipodia protrusion (arrows) and consequently fascin1 localization.

Cell Migration Assay

With the aim of finding out if the observed effect of fascin1 inhibitors on filopodia lamellipodium formation protrusion has a quantifiable effect on cell migration, MOCK basal condition, and migrastatin or imipramine-treated cells were investigated for their migration activity after 4-7 hours in vitro scratch.

FIG. 6 shows the cell migration assay for the three cell lines A) HCT-116, B) DLD-1, C) SW-480, D) Migration was calculated with respect to the control conditions for a slope between 4 and 7 h (lineal phase). *p<0.05, **p<0.01. As shown in FIG. 6, imipramine produces a remarkable inhibition of migration in all cell lines assayed (p<0.05). Except for SW-480, imipramine effect was more pronounced than migrastatin, especially for DLD-1. Cell migration was studied with the three cell lines by performing the wound healing assay in the presence of 5% FBS. Cancer colorectal cells (50,000 cells) were plated in low 35-mm-dishes with culture inserts (Ibidi, Martinsried, Germany). After appropriate cell attachment and monolayer formation (around for 24 h), inserts were then removed with sterile forceps to create a wound field of approximately 500 µm, according to the manufacturer protocol. Detached cells were gently removed with phosphate buffered saline (PBS, Dubelco) before the addition of drugs. Confluent cells were incubated in one of the following treatments: 100 µM migrastatin (AnalytiCon Discovery, cat. No. NP-006108), and 20 µM imipramine ((purchased via Molport, Letonia) and, control dishes that were incubated in the presence of 0.1% DMSO. Cells were then allowed to migrate in a cell culture incubator for 24 h. At 0, 3, 5 and 7 h (linear growth phase), 10 fields of the injury area were photographed with an inverted and phase contrast microscopy at ×10 magnification incorporating a CCD camera. For each timepoint, the area uncovered by cells was determined by an image processing free software analysis with Image J software program.

The migration speed of the wound closure is given as the percentage of the recovered area at each time point, relative to the initially covered area (0 h). The velocity of wound closure (%/h) was calculated according to the formula: Slope (%/h)=((% covered area t_x)−(% covered area t_0))/((tx−t_0)). Slopes are then expressed as percentages relative to control conditions.

Table 3 Shows the Reduction in Migration Upon Migrastatin and Imipramine Treatment on DLD1, SW-480 and HCT-116 Colorectal Cancer Cell Lines.

| Cell line | Treatment | Migration (%) | Standard Deviation (%) |
|---|---|---|---|
| DLD1 | MOCK | 100 | 0 |
|  | IMP | 23.2083448 | 12.21272854 |
|  | MGS | 67.90997002 | 5.189391673 |
| SW-480 | MOCK | 100 | 0 |
|  | IMP | 77.5217004 | 22.34697648 |
|  | MGS | 70.33726892 | 18.04369881 |
| HCT-116 | MOCK | 100 | 0 |
|  | IMP | 43.24797748 | 6.821640587 |
|  | MGS | 44.59324568 | 6.140935874 |

Transwell Invasion Assay

Figure 7:
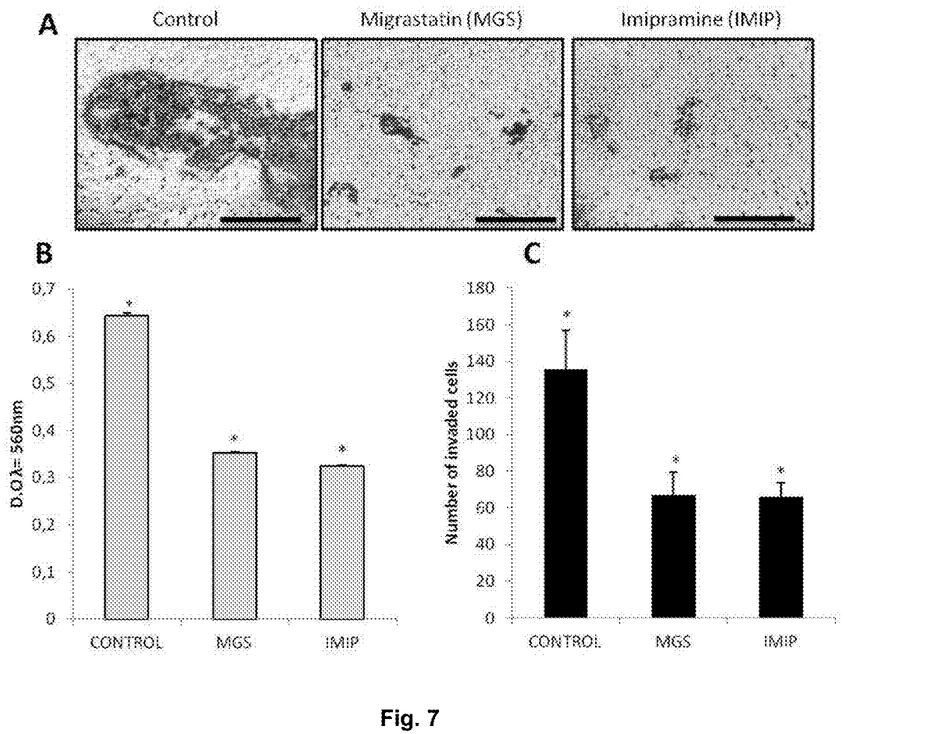
FIG. 7 shows how migrastatin and imipramine inhibit the cells invasive ability.

Tumor cell invasion not only involved the acquisition of migration properties but also the ability to degrade the extracellular matrix (ECM). For that reason, we performed a Transwell assay on Matrigel which resembles the ECM composition. The invasive capacities of HCT116 cells were determined using Cytoselect TM 24 Well Cell Invasion Assay (Basement Membrane Colorimetric Format) with coated Transwell chambers (8 µm pore size). Briefly, cells were resuspended with serum-free medium and treated with corresponding inhibitors (migrastatin 100 µM and, imipramine 20 µM). Cells ($9.5 \times 10^4$) were seeded into the upper chamber, and in the lower chamber 500 µL of DMEM containing 10% FBS were added. After 30 hours of incubation, cells that remained on the upper chamber were scraped away with a cotton swab, and cells that migrated to the bottom of the filter were stained with the cell stain solution. The number of invaded cells was photographed under an inverted phase contrast microscope and quantified D.O.D by a spectrophotometer at $\lambda=560$ nm. Also we analyzed the invasive cells using the Image J software. FIG.

7 shows the transwell invasion assay performed to evaluate HCT116 cells invasive ability. A) Invasiveness of cells after treatment with different drugs. Pictures were taken under an inverted phase contrast microscope. The magnification was ×200 and scale bars=50 μm. B) Quantification of the invasive cells D.O. by a spectrophotometer at A=560 nm. C) Number of invasive cells using the Image J software. Data are presented as mean±SD; compared with the control *P<0.01.

As shown in FIG. 7, both migrastatin and imipramine inhibit tumor cell migration of HCT-116, the effect of imipramine being slightly more evident than that of migrastatin.

Myoma Organotypic Invasion Model

Figure 8A:
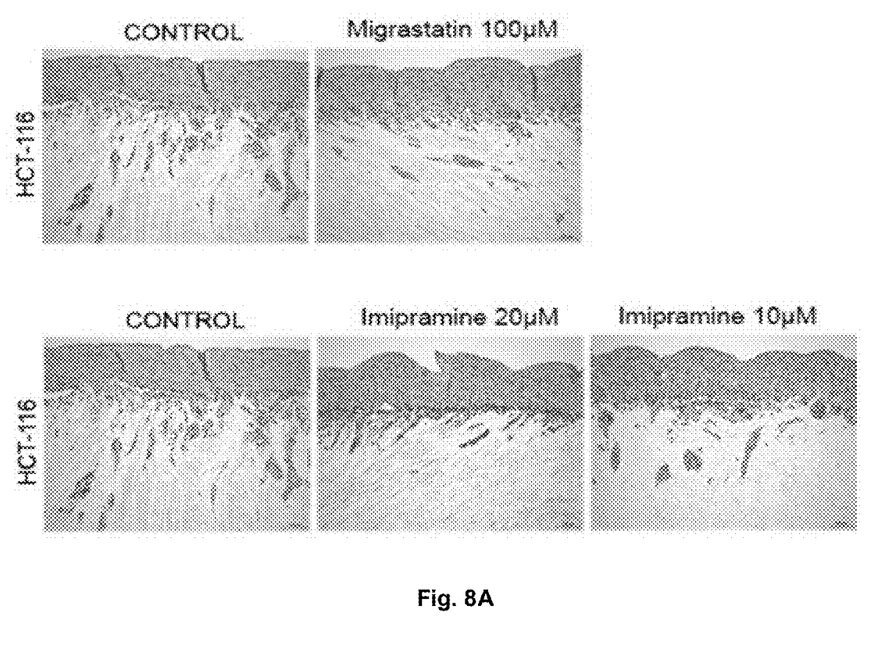
FIG. 8 shows how imipramine inhibits both depth (B) and area (C) of invasion of HCT-116 compared to control (exent to migrastatin) in a Myoma organotypic invasion model (A).
Figure 8B:
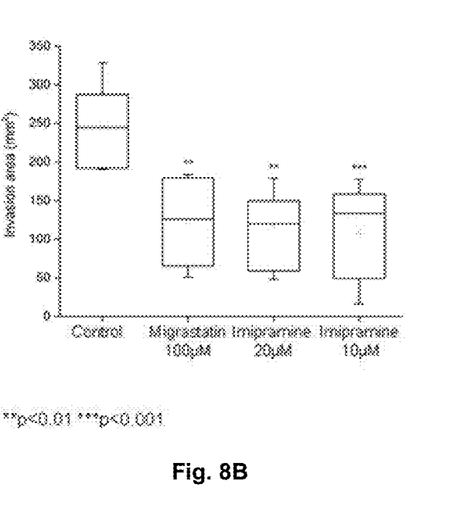
Figure 8C:
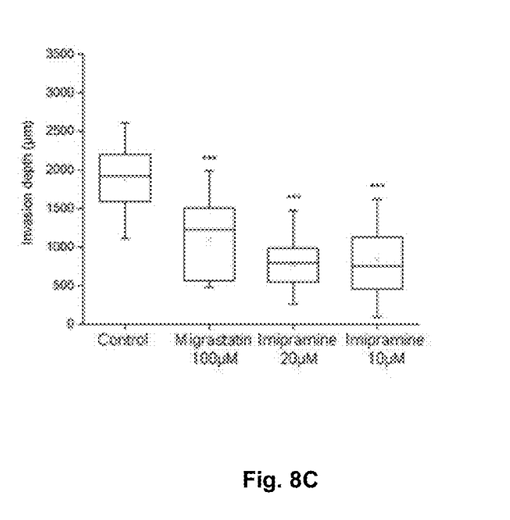

To improve the reliability of the experimental model compared to the real tumor microenvironment, cancer cell invasion was assessed in the myoma organotypic cultures and performed according to the previously published myoma model (Åström, P., Heljasvaara, R., Nyberg, P., Al-Samadi, A., & Salo, 2018). Briefly, uterine leiomyoma tissues were obtained from routine surgery after informed consent of the donors and their use approved by The Ethics Committee of the Oulu University Hospital. The myoma tissue was sliced into 5 mm and disks were made with an 8-mm biopsy punch (Kai Industries Co., Gifu, Japan). Myoma disks were pre-incubated in 100 μM MGS, 10 μM and 20 μM imipramine or 0.1% DMSO-DMEM treatments at +4° C. for 48 h. The myoma disks were placed into Transwell inserts (diameter 6.5 mm; Corning Incorporated, Corning, NY) and 700,000 cells in 50 μl of media were added on top of each myoma disk. The cells were allowed to attach overnight and the myoma disks were transferred onto uncoated nylon disks resting on curved steel grids in 12-well plates with 12 well plates with 1 ml of media plus migrastatin and imipramine in each well. The cancer cells were left to invade the myoma disks for 14 days, while changing the treatment media every 3 days. Subsequently the myoma discs were fixed with 4% neutral buffered formalin at room temperature for 24 h, and processed for histology. Six-μm sections were cut and stained with cytokeratin AE1/AE3 (M3515, Dako). Sections were documented at ×10 magnification, using the Leica DMRB microscope DFC 480 camera with the Leica application suite v3.8 (Leica Microsystems, Wetzlar, Germany). Image J v1.46o (National Institute of Health, Bethesda, MD, USA) was used to measure invasion areas and depths. Each treatment was performed in triplicate. FIG. 8 shows the myoma organotypic invasion model showing the effect of imipramine on HCT-116 colorectal cell line (A) on depth (B) and area (C) of invasion. As shown in FIG. 8 imipramine inhibits both depth and area of invasion of HCT-116 compared to control in a comparable extent to migrastatin.

In Vivo Assay on Zebra Fish Invasion Model

Finally, in order to find out whether the anti-invasive properties of imipramine could be extrapolable to an animal system, the well-established zebra fish larvae invasion model was used. A xenograft assay was carried out by stained with fluorescent CM-Dil (Vibrant, Invitrogen) two colorectal cancer cell lines (DLD-1 and HCT-116) and injected in zebra fish. The result obtained is referred to the percentage of cell invasion.

Figure 9:
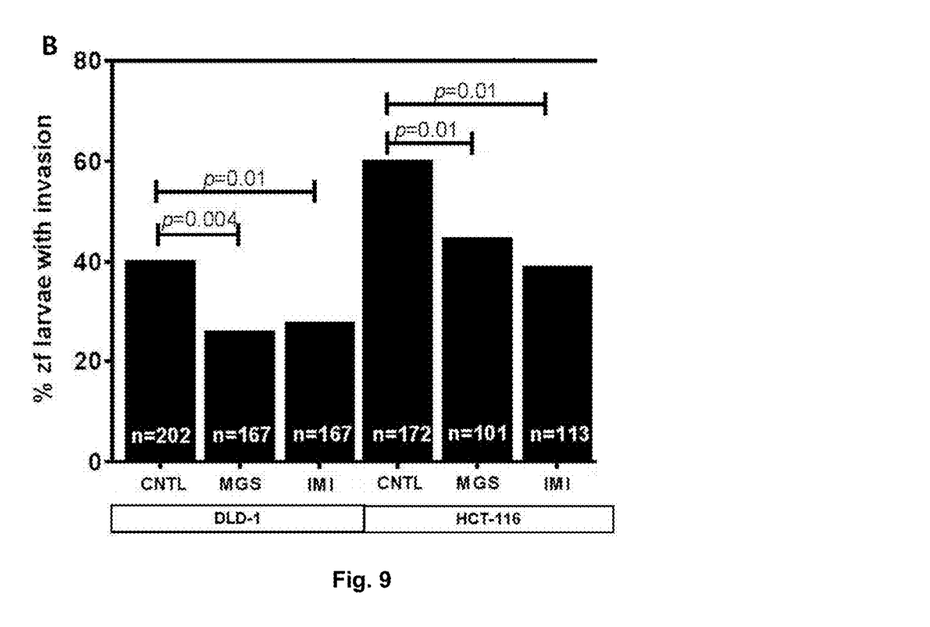
FIG. 9. Zebra fish invasion assays. (A) The images on the right show the localization of injected colorectal cancer cells (DLD-1 and HCT-116) into the yolk sac of zebra fish larvae (arrows). Left images show migration and invasion of cancer cells along the tail, outside the yolk sac (arrows). (B) The effect of imipramine (IMP) in diminishing cell invasion is evident comparing with control.
Figure 9A:
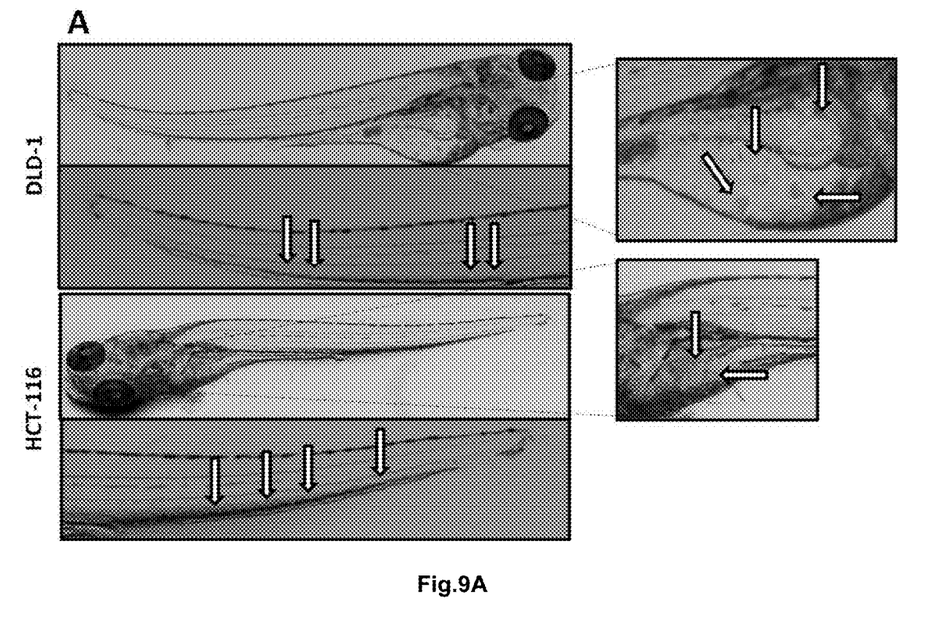

FIG. 9 shows the migration of colorectal cancer cell lines that can be visualized in the larvae of zebra fish. Injection and migration of different colorectal cancer cell lines in zebra fish model (A). Two colorectal cancer cell lines (DLD-1 and HCT-166) were treated with migrastatin and imipramine and injected in zebra fish larvae. The effect of imipramine (IMP) in diminishing cell invasion is evident compared to control treated with migrastatin (B).

Data Analysis

Data are expressed as mean±standard deviation (SD). Data were analyzed for statistical differences by the Student's t-test for paired and unpaired data after testing for normal distribution of the data. For in vitro experiments, one-way analysis of variance (ANOVA) was performed followed by a Tukey poshoc test to compare each group. Differences were considered significant at an error probability of Pp<0.05. SPSS 18.0 software was used for the rest of statistical analyses (SPSS, Inc, Chicago, Illinois, USA).

REFERENCES

Åström, P., Heljasvaara, R., Nyberg, P., Al-Samadi, A., & Salo, T. (2018). Human Tumor Tissue-Based 3D In Vitro Invasion Assays. *Methods in Molecular Biology* (Clifton, N.J.), 1731, 213-221.

Chen, L., Yang, S., Jakoncic, J., Zhang, J. J., & Huang, X. Y. (2010). Migrastatin analogues target fascin to block tumour metastasis. *Nature*. https://doi.org/10.1038/nature08978

Conesa-Zamora, P., García-Solano, J., García-García, F., Turpin, M. D. C., Trujillo-Santos, J., Torres-Moreno, D., . . . Pérez-Guillermo, M. (2013). Expression profiling shows differential molecular pathways and provides potential new diagnostic biomarkers for colorectal serrated adenocarcinoma. *International Journal of Cancer*, 132(2), 297-307. https://doi.org/10.1002/ijc.27674

García-Solano, J., Conesa-Zamora, P., Carbonell, P., Trujillo-Santos, J., Torres-Moreno D, D., Pagán-Gõmez, I., . . . Pérez-Guillermo, M. (2012). Colorectal serrated adenocarcinoma shows a different profile of oncogene mutations, MSI status and DNA repair protein expression compared to conventional and sporadic MSI-H carcinomas. *International Journal of Cancer*. https://doi.org/10.1002/ijc.27454

Gerhard Wolber, T. L. (2005). LigandScout: 3-D Pharmacophores Derived from Protein-Bound Ligands and Their Use as Virtual Screening Filters. *Journal of Chemical Information and Modeling*, 45(1), 160-169.

Hamilton, S. R. et al. (2010). Carcinoma of the colon and rectum. In, WHO classification of tumours of the digestive system. *In WHO Classification of Tumours, Volume 3 IARC WHO Classification of Tumours, No 3* Bosman, F. T., Carneiro, F., Hruban, R. H., Theise, N. D (IARC, p. 134).

Han, S., Huang, J., Liu, B., Xing, B., Bordeleau, F., Reinhart-King, C. A., . . . Huang, X.-Y. (2016). Improving fascin inhibitors to block tumor cell migration and  metastasis. *Molecular Oncology*, 10, 966-980. https://doi.org/10.1016/j.molonc.2016.03.006

Hashimoto, Y., Kim, D. J., & Adams, J. C. (2011). The roles of fascins in health and disease. *Journal of Pathology*. https://doi.org/10.1002/path.2894

Laiho, P., Kokko, A., Vanharanta, S., Salovaara, R., Sammalkorpi, H., Jarvinen, H., . . . Aaltonen, L. A. (2007). Serrated carcinomas form a subclass of colorectal cancer with distinct molecular basis. *Oncogene*, 26(2), 312-320. https://doi.org/10.1038/sj.onc.1209778

Machesky, L. M., & Lia., A. (2010). Fascin: Invasive filopodia promoting metastasis. *Communicative and Integrative Biology*. https://doi.org/10.4161/cib.3.3.11556

Stefanius, K., Ylitalo, L., Tuomisto, A., Kuivila, R., Kantola, T., Sirniö, P., . . . Mäkinen, M. J. (2011). Frequent mutations of KRAS in addition to BRAF in colorectal serrated adenocarcinoma. *Histopathology.* https://doi.org/10.1111/j.1365-2559.2011.03821.x Tan, V. Y., Lewis, S. J., Adams, J. C., & Martin, R. M. (2013). Association of fascin-1 with mortality, disease progression and metastasis in carcinomas: A systematic review and meta-analysis. *BMC Medicine,* 11(1), 1-17. https://doi.org/10.1186/1741-7015-11-52

Tuomisto, A., GarcÃ­a-Solano, J., SirniÃ¶, P., VÃ¶yrynen, J., PÃ©rez-Guillermo, M., MÃ¤kinen, M. J., & Conesa-Zamora, P. (2016). HIF-1α expression and high microvessel density are characteristic features in serrated colorectal cancer. *Virchows Archiv.* https://doi.org/10.1007/s00428-016-1988-8

The invention claimed is:

1. A method for the treatment of cancer mediated by fascin1 comprising administering to a subject in need thereof an effective amount of imipramine.
2. The method according to claim 1, wherein the fascin1 is overexpressed.
3. The method according to claim 1, wherein the cancer is colorectal cancer.
4. The method according to claim 3, wherein the colorectal cancer is serrated adenocarcinoma.
5. The method according to claim 3, wherein the colorectal cancer is selected from gastrointestinal stromal tumors, leiomyosarcomas or melanomas.

SEQUENCE LISTING

<160> NUMBER OF SEQ ID NOS: 4

<210> SEQ ID NO 1
<211> LENGTH: 21
<212> TYPE: DNA
<213> ORGANISM: Homo sapiens
<220> FEATURE:
<221> NAME/KEY: misc_feature
<223> OTHER INFORMATION: gene name FSCN1, 115F (ENSG00000075618), primer name 115F

<400> SEQUENCE: 1
tccacgcgcc agggtatgga c                                              21

<210> SEQ ID NO 2
<211> LENGTH: 20
<212> TYPE: DNA
<213> ORGANISM: Homo sapiens
<220> FEATURE:
<221> NAME/KEY: misc_feature
<223> OTHER INFORMATION: Gene name FSCN1, 116R (ENSG00000075618), primer name 116R Fragment size (bp) 121

<400> SEQUENCE: 2
acttgcccgt gtgggtacgg                                                20

<210> SEQ ID NO 3
<211> LENGTH: 20
<212> TYPE: DNA
<213> ORGANISM: Homo sapiens
<220> FEATURE:
<221> NAME/KEY: misc_feature
<223> OTHER INFORMATION: Gene name N2-ACTIN, (ENSG00000075624), primer name b-a b1gF

<400> SEQUENCE: 3
gagctacgag ctgcctgacg                                                20

<210> SEQ ID NO 4
<211> LENGTH: 21
<212> TYPE: DNA
<213> ORGANISM: Homo sapiens
<220> FEATURE:
<221> NAME/KEY: misc_feature
<223> OTHER INFORMATION: Gene name N2-ACTIN, (ENSG00000075624), primer name b-a b1gR Fragment size (bp) 120

<400> SEQUENCE: 4
gtagtttcgt ggatgccaca g                                              21

6. The method according to claim 3, wherein the colorectal cancer is metastatic colorectal cancer.

\* \* \* \* \*